United States Patent
Petasis et al.

(10) Patent No.: US 7,462,746 B2
(45) Date of Patent: Dec. 9, 2008

(54) AMINO POLYOLS AND AMINO SUGARS

(75) Inventors: Nicos A. Petasis, Hacienda Heights, CA (US); Ilia A. Zavialov, Princeton, NJ (US); Zubin D. Patel, Cerritos, CA (US)

(73) Assignee: University of Southern California, Los Angeles, CA (US)

( * ) Notice: Subject to any disclaimer, the term of this patent is extended or adjusted under 35 U.S.C. 154(b) by 765 days.

(21) Appl. No.: 10/405,922

(22) Filed: Apr. 1, 2003

(65) Prior Publication Data

US 2004/0053330 A1   Mar. 18, 2004

Related U.S. Application Data

(60) Continuation-in-part of application No. 09/699,076, filed on Oct. 27, 2000, now abandoned, which is a division of application No. 08/884,188, filed on Jun. 27, 1997, now Pat. No. 6,232,467, application No. 10/405,922, which is a continuation-in-part of application No. 09/425,498, filed on Oct. 22, 1999, now Pat. No. 6,602,817.

(60) Provisional application No. 60/369,544, filed on Apr. 1, 2002, provisional application No. 60/105,489, filed on Oct. 23, 1998, provisional application No. 60/020,741, filed on Jun. 28, 1996.

(51) Int. Cl.
C07C 215/10 (2006.01)
C07C 215/02 (2006.01)
C07C 215/00 (2006.01)

(52) U.S. Cl. .................. 564/507; 564/463; 564/503; 564/506

(58) Field of Classification Search ................ 564/507, 564/463, 503, 506
See application file for complete search history.

(56) References Cited

U.S. PATENT DOCUMENTS

| | | | |
|---|---|---|---|
| 4,442,099 A | 4/1984 | Nicolaou et al. | |
| 4,567,290 A | 1/1986 | Nicolaou et al. | |
| 4,710,521 A | 12/1987 | Soukup et al. | |
| 4,759,880 A | 7/1988 | Nicolaou et al. | |
| 5,087,790 A | 2/1992 | Petasis et al. | |
| 5,136,501 A | 8/1992 | Silverman et al. | |
| 5,177,046 A | 1/1993 | Savoca et al. | |
| 5,594,732 A | 1/1997 | Bell et al. | |
| 5,752,238 A | 5/1998 | Dedrick | |
| 5,756,789 A | 5/1998 | Bruce et al. | |
| 5,842,040 A | 11/1998 | Hughes et al. | |
| 5,845,265 A | 12/1998 | Woolston | |
| 5,870,717 A | 2/1999 | Wiecha | |
| 5,878,400 A | 3/1999 | Carter, III | |
| 5,878,423 A | 3/1999 | Anderson et al. | |
| 5,890,138 A | 3/1999 | Godin et al. | |
| 5,896,379 A | 4/1999 | Haber | |
| 5,946,467 A | 8/1999 | Pathakis et al. | |
| 6,030,715 A | 2/2000 | Thompson et al. | |
| 6,030,917 A | 2/2000 | Weinberg et al. | |
| 6,069,109 A | 5/2000 | Kao et al. | |
| 6,232,467 B1 | 5/2001 | Petasis et al. | |
| 6,259,699 B1 | 7/2001 | Opalka et al. | |
| 6,272,474 B1 | 8/2001 | Garcia | |
| 6,336,105 B1 | 1/2002 | Conklin et al. | |
| 6,336,138 B1 | 1/2002 | Caswell et al. | |
| 6,377,937 B1 | 4/2002 | Paskowitz | |
| 6,397,212 B1 | 5/2002 | Biffar | |
| 6,415,270 B1 | 7/2002 | Rackson et al. | |
| 6,427,132 B1 | 7/2002 | Bowman-Amuah | |
| 6,602,817 B1 | 8/2003 | Petasis | |
| 2003/0236423 A1 | 12/2003 | Petasis | |

FOREIGN PATENT DOCUMENTS

| | | | |
|---|---|---|---|
| EP | 0 736 509 A2 | 10/1996 | |
| EP | 0 736 509 B1 | 11/2001 | |
| JP | 4-46174 | * 2/1992 | |
| WO | WO 97/19415 | 5/1997 | |
| WO | WO 98/19259 | 5/1998 | |
| WO | WO 98/35469 | 8/1998 | |
| WO | WO 99/06913 | 2/1999 | |
| WO | WO 99/13417 | 3/1999 | |

OTHER PUBLICATIONS

Alexander et al., Tetrahedron Letter, vol. 37, No. 12, pp. 1961-1964, Mar. 1996.*
Kobayashi et al., Chem. Pharm. Bull., vol. 39, No. (10), pp. 2550-2555 (1991).*
Kaseda et al., Tetrahedron Letters, vol. 30, No. 34, pp. 4539-4542, 1989.*
Hatakeyama et al., Tetrahedron Letters, vol. 34, No. 46, pp. 7425-7428, 1993.*
Barrett et al., Tetrahedron, vol. 36, pp. 7857-7870 (1993).*
Poch et al., Tetrahedron Letters, vol. 34, pp. 7781-7784 (1993).*
Matsuura et al., Tetrahedron, vol. 49, No. 36, pp. 8211-8222, (1993).*
Canas et al., Tetrahedron, vol. 32, No. 47, pp. 6931-6934, (1991).*
Babine, R. E. and S.L. Bender., "Molecular Recognition of Protein-Ligand Complexes: Applications to Drug Design," *Chem. Rev.* 97:1359-1472 (1997).
Bhaley, G. et al., "Solid-Phase Synthesis of Diverse Tetrahydro-1,4-Benzodiazepine-2-ones," *Tetrahedron Letters* 38(48):8375-8378 (1997).
Bläser E. et al., "Asymmetric Steering of Oxa Diels—Alder Reactions with Silyloxydienes Employing Proline Esters as Chiral Auxiliary Groups," *Eur. J. Org. Chem.*, 329-333, (1999).

(Continued)

Primary Examiner—Mark L Shibuya
(74) Attorney, Agent, or Firm—Fish & Richardson P.C.

(57) ABSTRACT

Synthetic methods provide for the simple, efficient preparation of amino polyols and derivatives. The methods include a three-component reaction of a carbohydrates with organoboron compounds and primary or secondary amine derivatives. The resulting amino polyols can be transformed into amino sugars. In one implementation, the amine moiety is protected, and an alkenyl, aryl or heteroaryl moiety is cleaved to form the amino sugar. Amino polyols and amino sugars prepared according to the methods are also described.

19 Claims, No Drawings

OTHER PUBLICATIONS

Deloux, Laurent and Morris Srebnik "Asymmetric Boron-Catalyzed Reactions", *Chem. Rev.* 93:763-784, (1993).

Durantel. et al., "Study of the Mechanism of Antiviral Action of Iminosugar Derivatives against Bovine Viral Diarrhea Virus," *J. Virology* 75(19): 8987-8998, (2001).

Du Bois, et al., "Novel, Stereoselective Synthesis of 2-Amino Saccharides," *J. Am. Chem. Soc.* 119:3179-3180, 1997.

Evans, B.E. et al., "Design of Nonpeptidal Ligands for a Peptide Receptor: Cholecystokinin Antagonists," *J. Med. Chem.* 30:1229-1239 (1987).

Fletcher, M. D. and M.C. Campbell, "Partially Modified Retro-Inverso Peptides: Development, Synthesis, and Conformational Behavior," *Chem. Rev.*, 98:763-795, (1998).

Garro-Helion, et al., "Mild and Selective Palladium(0)-Catalyzed Deallylation of Allylic Amines. Allylamine and Diallylamine as Very Convenient Ammonia Equivalents for the Synthesis of Primary Amines," *J. Org. Chem.*, 58:6109-6113, (1993).

Golebiowski, A. and J. Jurczak, "α-Amino-β-hydroxy Acids in the Total Synthesis of Amino Sugars," *Synlett*, pp. 241-245, (Apr. 1993).

Guillier et al., "Linkers and Cleavage Strategies in Solid-Phase Organic Syntheis and Combinatorial Chemistry," *Chem. Rev.*, 100:2091-2157, (2000).

Hanessian, S. et al., "Design and Synthesis of Conformationally Constrained Amino Acids as Versatile Scaffolds and Peptide Manners," *Tetrahedron*, 53:12789-12854, (1997).

Hoyng, C.F. and A.D. Patel, "Aldehyde Components for Use in Four-Component Condensation ("4CC") UGI Reaction Peptide Synthesis," *Tetrahedron Lett.*, 21:4795-4798, (1980).

Humphrey, J.M. and A.R. Chamberlin, "Chemical Synthesis of Natural Product Peptides: Coupling Methods for the Incorporation on Noncoded Amino Acids into Peptides," *Chem. Rev.*, 97:2243-2266, (1997).

König et al., "Synthesis of N-tert-Alkylglyoxylic Acid Amides," *Synthesis*, pp. 1233-1234, (1993) [in German, English language abstract on 1st page of article].

Marx et al., "Synthetic Design for Combinatorial Chemistry. Solution and Polymer-Supported Synthesis of Polycyclic Lactams by Intramolecular Cyclization of Azomethine Ylides," *J. Am. Chem. Soc.*, 119:6153-6167, (1997).

Mehta et al., "Structure-Activity Relationship of a New Class of Anti-Hepatitis B Virus Agents," *Antimicrobial Agents and Chemotherapy*, 46(12):4004-4008 (2002).

Nicolaou et al., "Novel IBX-Mediated Process for the Synthesis of Amino Sugars and Libraries Thereof," *Angew. Chem. Int. Ed. Engl.*, 39:2525-2529, (2000).

Nicolaou, et al., "Lipoxins and Related Eicosanoids: Biosynthesis, Biological Properties, and Chemical Synthesis," *Angew. Chem. Int. Ed. Engl.* 30:1100-1116, (1991).

Noyori, R. (Ed.), "Enantioselective Addition of Organometallic Reagents to Carbonyl Compounds: Chirality Transfer, Multiplication, and Amplification," Chapter 5 in *Asymmetrical Catalysis in Organic Synthesis*, New York: John Wiley & Sons, Inc., pp. 255-297 (1994).

Nugent, William A., "Chiral Lewis Acid Catalysis. Enantioselective Addition of Azide to Meso Epoxides", *J. Am. Chem. Soc.*, 114(7): 2768-2769 (1992).

O'Donnell, Martin J. and J. Falmagne, "The Synthesis of Amino Acids via Organoboranes." *J. Chem. Soc. Chem. Commun.*, No. 17, pp. 1168-1169, (Sep. 1, 1985).

Petasis, N. A. and I.A. Zavialov, "The Boronic Acid Mannich Reaction: A New Method for the Synthesis of Geometrically Pure Allylamines." *Tetrahedron Letters*, 34(4):583-586, (1993).

Petasis, N.A. and I.A. Zavialov, "A New and Practical Synthesis of α-Amino Acids from Alkenyl Boronic Acids," *J. Am. Chem. Soc.*, 119(2):445-446, (1997).

"Scope and Editorial Policy," *Organometallics*, published by the American Chemical Society 21(1):13A, 14A (2002).

Serhan et al., "Novel Functional Sets of Lipid-derived Mediators with Antiinflammatory Actions Generated from Omega-3 Fatty Acids via Cyclooxygenase 2-Nonsteroidal Antiinfammatory Drugs and Transcellular Processing," *J. Exp. Med.* 192:1197-1204, (2000).

Thompson, L.A. and J.A. Ellman, "Synthesis and Applications of Small Molecular Libraries," *Chem. Rev.* 96:555-600 (1996).

Waki, M. and J. Meienhofer, "Peptide Synthesis Using the Four-Component Condensation (Ugi Reaction)," *J. Am. Chem. Soc.*, 99:6075-6082, (1977).

Yamamoto, Y. and N. Asao, "Selective Reactions Using Allylic Metals." *Chem. Rev.*, 93:2207-2293, (1993).

\* cited by examiner

AMINO POLYOLS AND AMINO SUGARS

CROSS REFERENCE TO RELATED APPLICATIONS

This application is a continuation-in-part of and claims priority to U.S. application Ser. No. 09/699,076, filed Oct. 27, 2000, now abandoned, which is a divisional of U.S. application Ser. No. 08/884,188, filed Jun. 27, 1997, issued as U.S. Pat. No. 6,232,467 B1 on May 15, 2001, which claims the benefit of Provisional Application No. 60/020,741, filed Jun. 28, 1996. This application is also a continuation-in-part of and claims priority to U.S. application Ser. No. 09/425,498, filed Oct. 22, 1999, now U.S. Pat. No. 6,602,817, which claims the benefit of Provisional Application No. 60/105,489, filed Oct. 23, 1998. This application also claims the benefit of Provisional Application No. 60/369,544, filed on Apr. 1, 2002. Each of these prior applications is incorporated by reference herein in its entirety.

STATEMENT REGARDING FEDERALLY SPONSORED RESEARCH

The U.S. Government may have certain rights in this invention pursuant to Grant No. GM45970 awarded by the National Institutes of Health.

BACKGROUND

This invention relates to amino polyols and amino sugars and methods for the preparation of such compounds.

Amino polyols, i.e., compounds containing an amine functionality as well as two or more hydroxyl groups, are present in the structures of several types of natural and designed bioactive molecules and continue to attract considerable interest in the development of new pharmaceuticals. An important type of amino polyols are the amino sugars, which constitute a major class of naturally occurring molecules and have important and diverse biological functions. (R. W. Jeanloz, "The Amino Sugars", Academic Press, New York, 1969.) Many types of amino sugars are naturally occurring, particularly as components of various antibiotics and other important biomolecules. Also, among the various carbohydrates, amino sugars play a major role in glycobiology as key components of glucoconjugates. (See, e.g., Sears, P.; Wong, C. -H. Angew. Chem. Int. Ed. Engl., 38:2300, 1999; Nicolaou, K. C. et al, Angew. Chem. Int. Ed. Engl., 38:2096, 1999.)

Although there are many known methods for the synthesis of amino sugars (for example: A. Golebiowski, J. Jurczak, Synlett 241, 1992; J. Du Bois, etal. J. Am. Chem. Soc. 119: 3179, 1997; K. C. Nicolaou, etal. Angew. Chem. Int. Ed. Engl., 39:2525, 2000), most of these have a number of drawbacks including the use of many protection and deprotection steps, use of toxic, hazardous or non-practical reagents, the need for anhydrous or anaerobic conditions, cumbersome isolation procedures, the requirement for multiple reaction steps, limited applicability to certain substitution patterns, and difficulty in controlling stereochemistry or isomeric purity.

In addition to the need to develop practical synthetic routes to the natural amino sugars, for which there is growing interest, there is also an increasing demand for new methods to prepare diverse non-natural derivatives. Such compounds can serve as building blocks in combinatorial chemistry, for the development of new pharmaceuticals and new agrochemicals.

SUMMARY

The invention provides practical and effective methods for the synthesis of various amino polyols and amino sugars. In general, the methods begin with the three-component reaction of carbohydrates with primary or secondary amines and organoboron derivatives to form amino polyols. In some embodiments, this process is followed by the conversion of the amine group to a suitably protected form, such as an ammonium salt, amide, sulfonamide or carbamate derivative and finally the cleavage of the organoboron substituent to generate a carbonyl group, thereby forming an amino sugar. The invention also provides amino polyols and amino sugars that can be prepared according to these methods.

In embodiments, the methods disclosed herein can be implemented to provide one or more of the following advantages. The methods are practical and can give the amino polyol and amino sugar products in pure form without the need for chromatographic purification. The methods typically proceed with very high stereoselectivity (up to more than 99% de and 99% ee). The methods can be simply performed, and generally require no hazardous chemicals or special precautions, making them suitable for the practical and convenient synthesis of many types of amino polyols and amino sugars.

The details of one or more embodiments of the invention are set forth in the description below. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. Other features, objects, and advantages of the invention will be apparent from the description, and from the claims.

DETAILED DESCRIPTION

Definitions:

As used in this specification, alkyl groups are straight-chained, branched or cyclic alkyl radicals containing up to about 20 carbons. Suitable alkyl groups may be saturated or unsaturated. Further, an alkyl may also be substituted one or more times on one or more carbons with substituents selected from the group consisting of C1-C6 alkyl, C3-C6 heterocycle, aryl, halo, hydroxy, amino, alkoxy and sulfonyl. Additionally, an alkyl group may contain up to 10 heteroatoms. Suitable heteroatoms include nitrogen, oxygen and sulfur.

As used in this specification, aryl groups are aromatic radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

General Description:

In one aspect, the invention provides methods for the synthesis of amino polyols, including amino sugars, from carbohydrates, amines and organoboron derivatives.

Suitable carbohydrates are compounds that contain an alkyl group substituted with at least two hydroxy groups, as well as at least one carbonyl group that exists in one of the following forms: aldehyde, ketone, lactol, hemiacetal, hemiketal, aminol or aminal. Suitable carbohydrates include those in an open chain form or in a heterocyclic form, such as a furanose or pyranose form. Carbohydrates can also be in an aldose or ketose form and may be monosaccharides, disaccharides, or oligosaccharides. Suitable carbohydrates include, but are not limited to, dihydroxyacetone and either enantiomer of: glyceraldehyde, erythrose, threose, erythrulose, ribose, arabinose, xylose, lyxose, ribulose, xylulose, glucose, mannose, allose, altrose, gulose, idose, galactose, talose, psicose, fructose, sorbose or tagatose, as well as disaccharides, such as maltose, cellobiose, melibiose, and lactose. One or more hydroxyl groups in the carbohydrate can be protected with a suitable protecting group (e.g., in the form —OR, where R is alkyl, aryl, heteroaryl, silyl, acyl, alkoxyacyl or aminoacyl). Carbohydrates can also be deoxy-carbohydrates in which one or more hydroxyl groups are replaced with a hydrogen.

Also suitable for use in the methods of the present invention are carbohydrate derivatives, which include derivatives of the above carbohydrates having one or more hydroxyl groups replaced with a substituent selected from a group that includes: alkyl, alkenyl, alkynyl, allenyl, aryl, heteroaryl, alkoxy, silyloxy, acyl, acyloxy, oxo, carboxy, carboxyalkyl, carboxyaryl, carboxamido, dialkylamino, acylamino, cyano, sulfonylamino, carbamate, acetal, ketal, borate, boronate, or 3-7 membered heterocycle. Carbohydrates include carbohydrate derivatives that have at least one hydroxyl group (CHOH) replaced with its higher oxidized form, such as aldehyde (CHO), ketone (CO) or carboxyl group (COOH).

Primary or secondary amines include compounds of the general formula $R^1R^2NH$. As used in this specification, the substituents $R^1$ and $R^2$ can include hydrogen, alkyl, aryl, heteroaryl, hydroxy, alkoxy, acyl, carboxyalkyl, carboxamido, alkylamino, dialkylamino, acylamino, silyl, phosphinyl, sulfonyl, sulfinyl, alkylsulfonate. Further, the substituents $R^1$ and $R^2$ may be joined together to form one or more rings of 2 to 20 atoms. The amine component may also be part of an amino acid or a peptide derivative.

Suitable organoboron derivatives include compounds having a boron atom connected to at least one alkyl, alkenyl, alkynyl, allenyl, aryl or heteroaryl group. The remaining substituents attached to the boron atom can include, e.g., hydroxy, alkoxy, aryloxy, halo, amino, alkylamino, dialkylamino, alkyl aryl or heteroaryl.

The amino polyol products are compounds that contain an alkyl group substituted with at least one amino group as well as at least two hydroxy groups. The amino group can be primary ($NH_2$), secondary ($R^1NH$) or tertiary ($R^1R^2N$), or it can be an ammonium salt ($R^1R^2R^3N^+$). The substituents $R^1$, $R^2$ and $R^3$ can include hydrogen, alkyl, aryl, hydroxy, alkoxy, acylalkyl, carboxyalkyl, carboxamido, alkylamino, dialkylamino, acylamino, silyl, phosphinyl, sulfonyl, sulfinyl, alkylsulfonate. Further, the substituents $R^1$, $R^2$ and $R^3$ can be joined together to form one or more rings of 2 to 20 atoms. The amino group can also be part of an amino acid or a peptide derivative. The hydroxy groups can be in an unprotected form (OH) or in a protected form (OR), where R can include, for example, alkyl, aryl, silyl, acyl, alkoxyacyl or aminoacyl.

The amino sugar products are compounds that contain an alkyl group substituted with at least one amino group, at least two hydroxy groups, as well as at least one carbonyl group that exists in one of the following forms: aldehyde, ketone, carboxylic acid, carboxylic ester, lactone, lactol, hemiacetal, hemiketal, aminol, aminal, amide or lactam. The amino group can be primary ($NH_2$), secondary ($R^1NH$) or tertiary ($R^1R^2N$), or it can be an ammonium salt ($R^1R^2R^3N^+$). The substituents $R^1$, $R^2$ and $R^3$ can include hydrogen, alkyl, aryl, hydroxy, alkoxy, acyl, acylalkyl, carboxyalkyl, carboxamido, alkylamino, dialkylamino, acylamino, silyl, phosphinyl, sulfonyl, sulfinyl, alkylsulfonate. Further, the substituents $R^1$, $R^2$ and $R^3$ can be joined together to form one or more rings of 2 to 20 atoms. The amino group can also be part of an amino acid or a peptide derivative. The hydroxy groups can be in an unprotected form (OH) or in a protected form (OR), where R can include, for example, alkyl, aryl, silyl, acyl, alkoxyacyl and aminoacyl. The amino sugar can also contain additional substituents, including hydrogen, alkyl, alkenyl, alkynyl, allenyl, aryl, alkoxy, silyloxy, acyl, acyloxy, oxo, carboxy, carboxyalkyl, carboxyaryl, carboxamido, dialkylamino, acylamino, cyano, sulfonylamino, carbamate, acetal, ketal, borate, boronate, or 3-7 membered heterocycle. In some embodiments, the amino sugar can also contain as a substituent a carbohydrate moiety.

Method for Preparing Amino Polyols:

In one embodiment, illustrated in Scheme 1, amino polyols of formula (4) are prepared in a three-component reaction among a carbohydrate (1a or 1b), a primary or secondary amine (2), and an organoboron derivative (3).

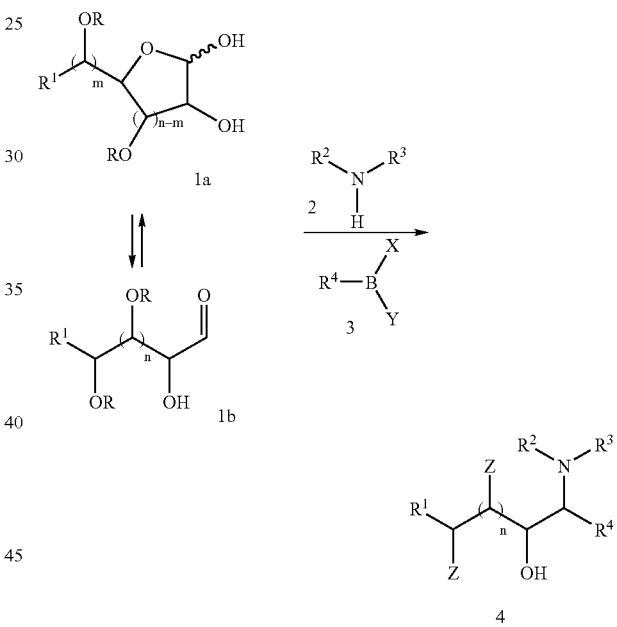

Scheme 1

In structures 1-4, n and m are integers from 0-4 and n is greater than or equal to m. R is hydrogen, alkyl, aryl, silyl, acyl, alkoxyacyl, aminoacyl or a carbohydrate. $R^1$ is hydrogen, alkyl, alkenyl, alkynyl, allenyl, aryl or heteroaryl. $R^2$ and $R^3$ are hydrogen, alkyl, aryl, hydroxy, alkoxy, acyl, carboxyalkyl, carboxamido, alkylamino, dialkylamino, acylamino, silyl, phosphinyl, sulfonyl, sulfinyl, or alkylsulfonate, provided that $R^2$ and $R^3$ can be joined together to form one or more rings of 2 to 20 atoms, and that the amine component (2) can also be part of an amino acid or a peptide derivative. $R^4$ is alkenyl, alkynyl, allenyl, aryl or heteroaryl, provided that where $R^4$ is allyl or allenyl, $R^4$ can exist in a different isomeric form in the organoboron derivative (3) and in the product (4). X and Y are hydroxy, alkoxy, aryloxy, amino, alkylamino, or dialkylamino, provided that X and Y can also be joined together forming a ring of 3 to 7 atoms. In particular embodiments, one of the three components can be attached to a polymer or to a solid support. In some embodiments, the product amino polyol is formed in predominantly one stereoisomer having the amino group in an anti-relationship to the adjacent hydroxyl group.

In other embodiments, the organoboron component can include molecules containing a fourth boron substituent that can be hydroxy, alkoxy, dialkylamino and halo. An example of such organoboron derivatives are the trifluoroborates ($R^4BF_3$).

The carbohydrate component can include substituted carbohydrates having one or more modifications. Thus, the carbohydrate hydroxy groups other than the anomeric hydroxyl group may be in an unprotected form (OH) or in a protected form (OR), where R can be alkyl, aryl, silyl, acyl, alkoxyacyl and aminoacyl. One or more carbohydrate hydroxyl groups other than the anomeric hydroxyl group may be replaced with a substituent that is a carbohydrate moiety (such as a disaccharide or an oligosaccharide). One or more carbohydrate hydroxyl groups other than the anomeric hydroxyl group may be replaced with a substituent that can be hydrogen, alkyl, alkenyl, alkynyl, allenyl, aryl, alkoxy, silyloxy, acyl, acyloxy, oxo, carboxy, carboxyalkyl, carboxyaryl, carboxamido, dialkylamino, acylamino, cyano, sulfonylamino, carbamate, acetal, ketal, borate, boronate, or 3-7 membered heterocycle. One or more carbohydrate hydroxyl groups (CHOH) other than the anomeric hydroxyl group, may be replaced with a corresponding higher oxidized form, such as aldehyde (CHO), ketone (CO) or carboxyl group (COOH).

The reaction illustrated in Scheme 1 can proceed directly in a variety of solvents, including water, alcohols, ethers, chlorinated hydrocarbons and acetonitrile. Suitable solvents are those that can dissolve at least two of the three components. A typical solvent is methanol or ethanol. In some implementations, the reaction can be promoted by adding Lewis acids, such as compounds containing electron-deficient atoms including boron, a lanthanide, silicon, tin, titanium and zinc.

In a typical procedure, the reaction proceeds in a single step. The reactants are combined in approximately equimolar amounts in the solvent, and maintained at a temperature between about 0° C. and the reflux temperature of the solvent, often between about 25° C. and about 75° C., until the reaction is complete. The course of the reaction can be followed by any standard method, including thin-layer chromatography and HPLC. In general, the reaction is conducted for about 1 to about 72 hours, often for about 12 to about 24 hours. Product isolation usually involves acid-base extraction and typically gives fairly pure products which in many cases can be purified by recrystallization, without the need for chromatography.

If desired, the product amino polyols of formula (4) can be subsequently transformed to form new derivatives, such as amino sugars as will be described next.

Method for Preparing Amino Sugars:

In another aspect, outlined in Scheme 2, the invention provides a synthetic route to amino sugars (7, 8, or 9) from amino polyols prepared according to Scheme 1 as described above. Following the reaction to produce the amino polyol of formula 4, as described in Scheme 1 above, compound 4 can be directly converted to an amino sugar 8, by converting substituent $R^4$ to a carbonyl group.

For example, if substituent $R^4$ is alkenyl, alkynyl, or allenyl, ozonolysis or other oxidative cleavage can directly form the carbonyl group. Alternatively, the amine group is first replaced with a suitable protected form, such as an ammonium salt (5), an amide, a sulfonamide, a carbamate, or other amine-stabilizing derivative (6). Oxidative (or other suitable) cleavage of substituent $R^4$ (derived from the organoboron compound as described above) gives the amino sugar product (7) or (9), as illustrated below in Scheme 2.

In general, the amino sugar products have the same stereochemistry as the amino polyol precursors (4) and can exist either in an open form (7a, 8a, 9a) or the corresponding furanose or pyranose forms (7b, 8b, 9b) as anomeric mixtures.

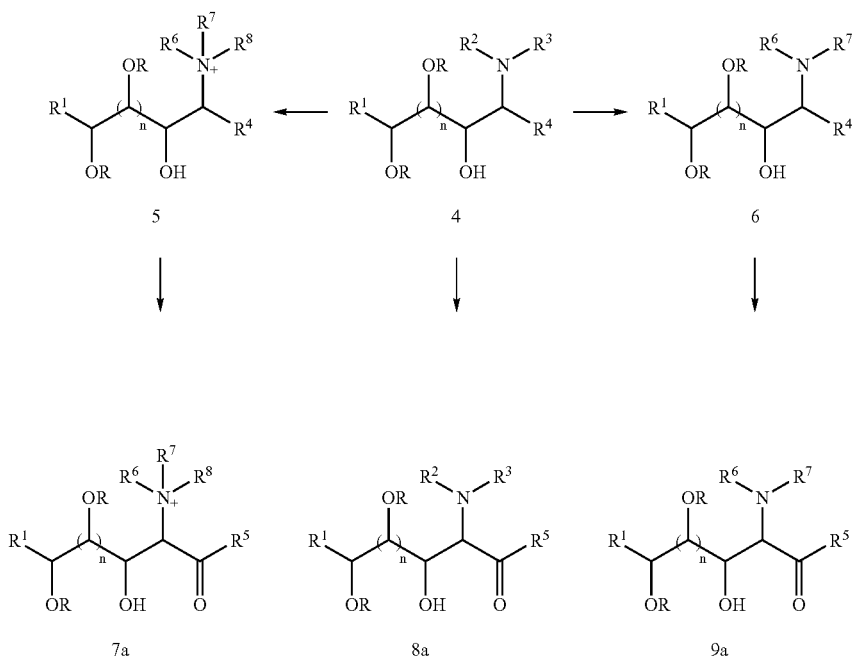

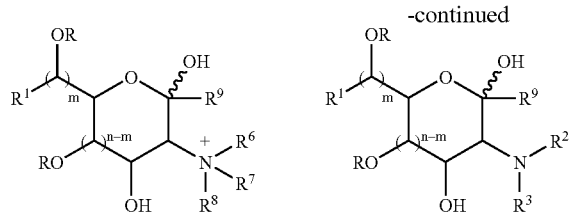
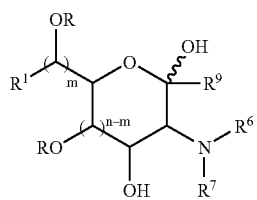

7b    8b    9b

In structures 4-9, n, m and substituents R, and $R^1$ through $R^4$ are defined as in Scheme 1, above. $R^5$ is hydrogen, alkyl, aryl, heteroaryl, acyl, hydroxy, alkoxy, carboxamido, alkylamino, or dialkylamino. $R^6$ and $R^7$ are hydrogen, acyl, alkoxyacyl, aminoacyl, carbamate, sulfonyl, sulfinyl, phosphonate or sulfonate, provided that $R^6$ and $R^7$ can be the same as substituents $R^2$ or $R^3$ and further provided that $R^6$ and $R^7$ can be joined together to form one or more rings of 2 to 20 atoms. $R^8$ is hydrogen, alkyl or acyl. $R^9$ is hydrogen, alkyl, alkenyl, alkynyl, allenyl, aryl, heteroaryl, acyl, carboxyalkyl, or carboxyaryl. In some embodiments, the product amino sugar is formed in predominantly one stereoisomer having the amino group in an anti-relationship to the adjacent hydroxyl group. The direct conversion of amino polyol 4 to amino sugar 8 is possible when the transformation of substituent $R^4$ to a carbonyl does not involve conditions that are incompatible with the amine group. For example, if this process involves acid or base hydrolysis of substituent $R^4$, simple amine substituents, such as alkyl or aryl are compatible. Alternatively, if an oxidative method is used for the conversion of substituent $R^4$ to a carbonyl, then the amine substituents must be stable to the reactions used. For example this would be possible if $R^2$ or $R^3$ are acyl, alkoxyacyl (carbamate), aminoacyl, sulfonyl, sulfinyl, phosphinyl, phosphonate, etc.

In one embodiment of the process described in Scheme 2, the amino polyol 4 is first converted to an ammonium salt (5) by treatment with acid or other electrophile, such as a Lewis acid, or by treatment with an acylating agent, such as an acyl halide. Alternatively, the amine moiety is protected in the form of an amide, carbamate, sulfonamide, phosphonamide, with or without replacement of substituents $R^2$ and $R^3$. Following such protection of the amine in the form of formula 5 or 6, substituent $R^4$ is then subjected to oxidative or other cleavage to generate a carbonyl group, thereby forming an amino sugar. For example if substituent $R^4$ is alkenyl, alkynyl, allenyl, or heteroaryl (e.g., furyl), this can be accomplished by ozonolysis, while if substituent $R^4$ is aryl or heteroaryl (e.g., furyl) this can also be accomplished with oxidation, such as treatment with a ruthenium catalyst and sodium periodate.

In some embodiments, the methods feature the use of di-p-anisyl-methylamine, which is cleaved under acidic conditions prior to an oxidative conversion of substituent $R^4$ to a carbonyl.

In other embodiments, the methods can feature the use of allylamines as the amine components. In this case the allyl moieties can be easily removed from the N-atom using known processes, such as palladium catalysis (S. Lemaine-Audoire, et al, Tetrahedron Lett. 36:1267, 1995). In this manner it is possible to use acidic conditions to purify the initial intermediates, resulting in higher overall yields and improved product purities.

The processes outlined in Scheme 2 can be performed by using conditions known to those skilled in the art.

Amino Polyols:

In another aspect, the invention provides amino polyol derivatives of formula 10.

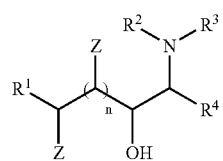

10 wherein:
n is an integer from 0-4;
$R^1$ is hydrogen, alkyl, alkenyl, alkynyl, allenyl, aryl or heteroaryl;
$R^2$ and $R^3$ are independently hydrogen, alkyl, aryl, hydroxy, alkoxy, carboxyalkyl, carboxamido, alkylamino, dialkylamino, acylamino, silyl, phosphinyl, sulfonyl, sulfinyl, or alkylsulfonate, provided that $R^2$ and $R^3$ can be joined together to form one or more rings of 2 to 20 atoms;
$R^4$ is alkenyl, alkynyl, allenyl, aryl or heteroaryl; and
the Z substituents are independently selected from the group consisting of hydroxy, hydrogen, alkyl, alkenyl, alkynyl, allenyl, aryl, acyl, oxo, carboxy, carboxyalkyl, carboxyaryl, carboxamido, dialkylamino, acylamino, cyano, sulfonylamino, carbamate, acetal, ketal, borate, boronate, 3-7 membered heterocycle, and —OR, where R is alkyl, aryl, silyl, acyl, alkoxyacyl or aminoacyl, provided that R can be a carbohydrate or oligosaccharide, and provided that at least one Z substituent must be hydroxy or —OR.

The amino polyol derivatives of formula 10 can be made according to the methods described above.

Amino Sugars and Their Derivatives:

In another aspect, the invention provides amino sugar derivatives of formula 11 or formula 12, that can exist either in their open form (11a, 12a), and/or in their furanose or pyranose forms (11b, 12b).

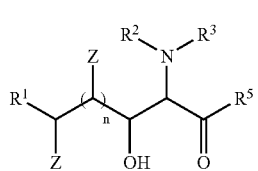

11a

-continued

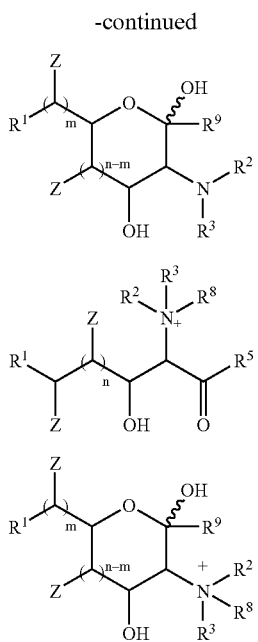

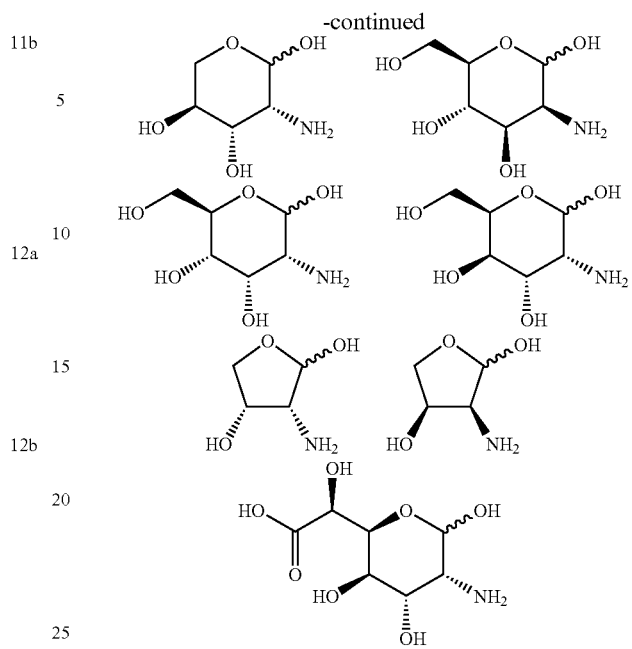

wherein:
   n is an integer from 0-4;
   R¹ is hydrogen, alkyl, alkenyl, alkynyl, allenyl, aryl or heteroaryl;
   R² and R³ are independently hydrogen, alkyl, aryl, hydroxy, alkoxy, carboxyalkyl, carboxamido, alkylamino, dialkylamino, acylamino, silyl, phosphinyl, sulfonyl, sulfinyl, or alkylsulfonate, provided that R² and R³ can be joined together to form one or more rings of 2 to 20 atoms;
   R⁵ is hydrogen, alkyl, aryl, heteroaryl, acyl, hydroxy, alkoxy, carboxamido, alkylamino, or dialkylamino;
   R⁸ is hydrogen, alkyl or acyl;
   R⁹ is hydrogen, alkyl, alkenyl, alkynyl, allenyl, aryl, heteroaryl, acyl, or carboxyalkyl; and
   the Z substituents are independently selected from the group consisting of hydroxy, hydrogen, alkyl, alkenyl, alkynyl, allenyl, aryl, acyl, oxo, carboxy, carboxyalkyl, carboxyaryl, carboxamido, dialkylamino, acylamino, cyano, sulfonylamino, carbamate, acetal, ketal, borate, boronate, 3-7 membered heterocycle, and —OR, where R is alkyl, aryl, silyl, acyl, alkoxyacyl or aminoacyl, provided that R can be a carbohydrate or oligosaccharide, and provided that at least one Z substituent must be hydroxy or —OR.

Scheme 3 shows selected types of amino sugars that can be readily made with the present invention in high stereochemical purity, as a mixture of anomers. A variety of derivatives, such as amine salts, amides, carbamates, and sulfonates of these compounds can also be made from these amino sugars.

Advantages and Improvements Over Existing Technology

Although there are many known methods for the synthesis of amino sugars, due to the vital importance of these compounds and the many shortcomings of existing methods, any conceptually new and practical method in this are is of special significance. The present methods can be implemented to offer one or more advantages over existing methods, including:

1. Practicality. The reactions can be done in alcohol or aqueous solvents at ambient temperature without using any toxic, hazardous or corrosive materials.

2. Unlike other methods which involve multi-step manipulations and the extensive use of protective groups, the methods disclosed herein offer direct asymmetric construction of amino polyols and amino sugars from simple building blocks.

3. The present methods involve a smaller number of synthetic steps than most existing methods. Starting materials are generally either commercially available or can be readily prepared from commercially available reagents.

4. Product isolation and purification can be much easier than with existing methods. In most cases, the product can be purified by recrystallization, without the need for laborious purification procedures, such as distillation or chromatography.

EXAMPLES

The following examples are provided for purposes of illustration and are not intended to limit the invention in any way. Representative experimental procedures and structural data of the obtained products are given in the examples. Efforts have been made to ensure accuracy with respect to numbers used (e.g., amounts, temperature, etc.) but some experimental errors and deviations should be accounted for. Unless indicated otherwise, parts are parts by weight, molecular weight Scheme 3

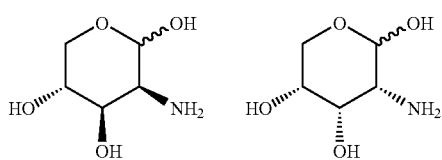

Example 1

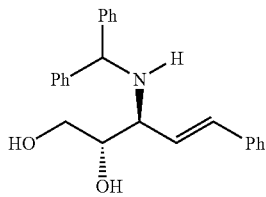

(R)-Glyceraldehyde (520 mg, ca. 75% in water, ca. 4.33 mmol) was dissolved in EtOH (15 mL) and to this solution was added aminodiphenylmethane (793 mg, 4.33 mmol), followed by (E)-2-phenylethenyl boronic acid (652 mg, 4.4 mmol). The reaction flask was sealed with a plastic stopper and the reaction mixture was vigorously stirred for 24 hours at ambient temperature. After the removal of volatiles, the residue was suspended in 6 N hydrochloric acid (20 mL) and heated with vigorous stirring at 60° C. for 1 hour. After that time, the solution was cooled and filtered. The precipitate on the filter was washed with cold water (2×10 mL), ethylacetate (3×20 mL) and dried to give 1201 mg of pure product (77% yield, >99% de, >99% ee). $^1$H NMR (250 MHz, CD$_3$OD) δ 7.30-7.65 (m, 15H), 6.60 (d, J=16 Hz, 1H), 6.33 (dd, J=16 Hz, 8.5 Hz, 1H), 5.59 (s, 1H), 4.18 (m, 1H), 3.93 (dd, J=8.5 Hz, 3.0 Hz, 1H), 3.57 (dd, J=10.9 Hz, 5.6 Hz, 1H), 3.40 (dd, J=10.9 Hz, 7.6 Hz, 1H). $^{13}$C NMR (63 MHz, C$_6$D$_6$) δ 144.8, 143.3, 137.1, 134.0, 129.0, 128.8, 128.7, 128.1, 127.9, 127.7, 127.4, 127.3, 126.8, 74.2, 65.2, 64.0, 61.5.

The anti-stereochemistry of the product was established as shown below, by hydrogenation in the presence of Boc$_2$O, followed by oxidation to form (S) homophenyl alanine, which was matched with an authentic material, using HPLC or NMR of the corresponding Mosher amide derivatives.

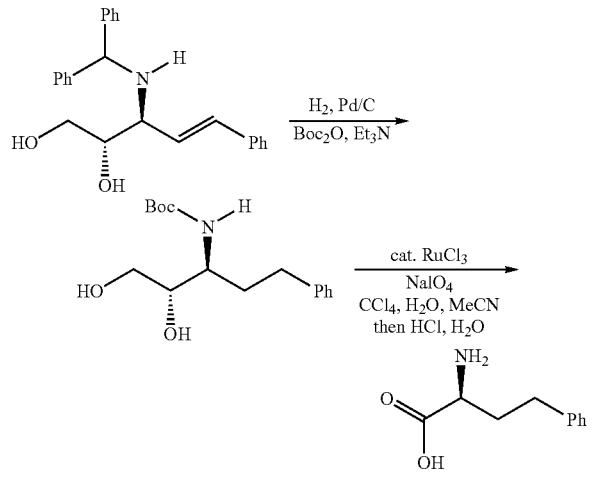

Example 2

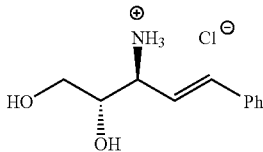

Prepared similarly to Example 1, using di(p-anisyl)methyl amine followed by acid cleavage in 78% yield for 2 steps, >99% de and ee. $^1$H NMR (250 MHz, CD$_3$OD) δ 7.25-7.51 (m, 5H), 6.82 (d, 16.0 Hz, 1H), 6.30 (dd, J=16.0 Hz, 8.8 Hz, 1H), 4.08 (dd, J=8.8 Hz, 3.4 Hz, 1H), 3.92 (m, 1H), 3.58 (m, 2H). $^{13}$C NMR (63 MHz, CD$_3$OD) δ 138.7, 129.8, 129.7, 129.2, 127.9, 121.0, 72.2, 64.0, 57.4.

Example 3

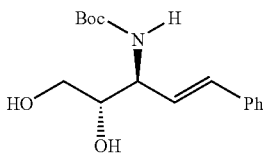

Prepared by protection with Boc$_2$O of the product of Example 2 in 89% yield, >99% de and ee. $^1$H NMR (360 MHz, CD$_3$OD) δ 7.18-7.41 (m, 5H), 6.58 (d, J=15.7 Hz, 1H), 6.27 (dd, J=15.7 Hz, 7.1 Hz, 1H), 4.27 (m, 1H), 3.68 (m, 1H), 3.58 (m, 2H), 1.45 (s, 9H). $^{13}$C NMR (90 MHz, CD$_3$OD) δ 157.8, 138.3, 133.1, 129.5, 128.5, 127.5, 127.4, 80.4, 75.2, 64.6, 56.1, 28.8.

Example 4

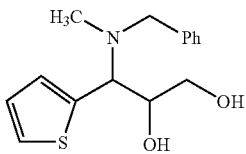

(DL)-Glyceraldehyde (100 mg, 1.11 mmol) was dissolved in EtOH (10 mL) and to this solution was added N-benzyl methylamine (134 mg, 1.11 mmol), followed by 2-thiophene boronic acid (143 mg, 1.12 mmol). The reaction flask was sealed with a plastic stopper and the reaction mixture was vigorously stirred for 24 hours at ambient temperature. After the removal of volatiles, the residue was redissolved in dichloromethane and purified by flash chromatography on silica gel using dichloromethane-methanol (800:70) as the eluent to give 246 mg of pure product (80% yield, >99% de). $^1$H NMR (360 MHz, acetone-d$_6$) δ 7.12-7.49 (m, 8H), 4.20 (m, 1H), 3.92 (d, J=7.7 Hz, 1H), 3.65 (m, 2H), 3.61 (d, J=13.2 Hz, 1H), 3.40 (d, J=13.2 Hz, 1H), 2.14 (s, 3H). $^{13}$C NMR (63 MHz, acetone-d$_6$) δ 140.2, 139.0, 129.6, 129.0, 128.0, 127.7, 126.9, 125.3, 72.3, 66.3, 66.1, 59.9, 38.4.

Example 5

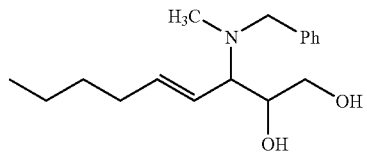

The reaction was performed as in Example 4 using hexenyl boronic acid. The product was obtained in 73% yield, >99% de. $^1$H NMR (360 MHz, acetone-d$_6$) δ 7.25-7.35 (m, 5H), 5.69 (dt, J=15.4 Hz, 5.4 Hz, 1H), 5.47 (dd, J=15.4 Hz, 9.6 Hz, 1H), 3.84 (m, 1H), 3.68 (d, J=13.4 Hz, 1H), 3.60 (dd, J=10.7 Hz, 5.6 Hz, 1H), 3.51 (dd, J=10.7 Hz, 6.1 Hz, 1H), 3.43 (d, J=13.4 Hz, 1H), 2.90 (dd, J=9.6 Hz, 8.0 Hz, 1H), 2.18 (s, 3H), 2.05 (m, 2H), 1.8 (m, 4H), 0.9 (t, J=6.9 Hz, 3H). $^{13}$C NMR (63 MHz, acetone-d$_6$) δ 140.5, 137.3, 129.7, 129.0, 127.6, 125.5, 71.8, 69.6, 66.8, 59.7, 38.5, 33.0, 32.4, 22.8, 14.2.

Example 6

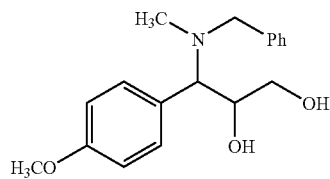

The reaction was performed as in Example 4, giving the product in 72% yield, >99% de. $^1$H NMR (250 MHz, CDCl$_3$) δ 6.98-7.45 (m, 9H), 4.35 (m, 1H), 3.86 (s, 3H), 3.79 (d, J=5.7 Hz, 2H), 3.70 (d, J=9.4 Hz, 1H), 3.56 (d, J=13.1 Hz, 1H), 3.38 (d, J=13.1 Hz, 1H), 2.21 (s, 3H). $^{13}$C NMR (63 MHz, CDCl$_3$) δ 159.1, 138.2, 130.8, 128.9, 128.4, 127.2, 125.5, 113.6, 70.6, 68.4, 66.8, 59.4, 55.1, 37.9.

Example 7

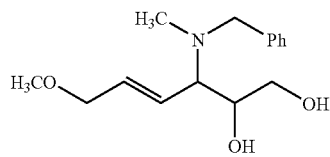

The reaction was performed as in Example 4, giving the product in 67% yield, >99% de. $^1$H NMR (250 MHz, acetone-d$_6$) δ 7.25-7.51 (m, 5H), 5.82 (ddt, J=15.3 Hz, 8.6 Hz, 1.3 Hz, 1H), 5.67 (dt, J=15.3 Hz, 5.5 Hz, 1H), 3.96 (dd, J=5.5 Hz, 1.3 Hz, 2H), 3.87 (m, 1H), 3.74 (d, J=13.3 Hz, 1H), 3.62 (dd, J=10.6 Hz, 5.5 Hz, 1H), 3.51 (dd, J=10.6 Hz, 6.2 Hz, 1H), 3.48 (d, J=13.3 Hz, 1H), 3.29 (s, 3H), 3.07 (dd, J=8.6 Hz, 7.5 Hz, 1H), 2.20 (s, 3H). $^{13}$C NMR (90 MHz, CDCl$_3$) δ 137.9, 134.5, 129.0, 128.6, 127.5, 125.7, 72.3, 69.4, 68.9, 66.5, 59.4, 58.2, 38.1.

Example 8

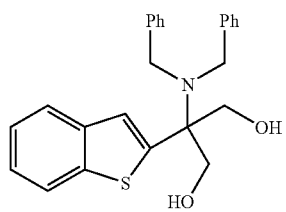

To a suspension of dihydroxy acetone (90 mg, 1 mmol) in ethyl alcohol (7 mL) was added dibenzylamine (197 mg, 1 mmol), followed by benzo[b]thiophene-2-boronic acid (178 mg, 1 mmol). The reaction mixture was stirred vigorously for 6 hours at ambient temperature and the precipitated product was isolated by filtration, washed with cold ethyl alcohol (2×10 mL) and dried to give the product, (250 mg 62% yield). $^1$H NMR (360 MHz, acetone-d$_6$) δ 7.01-8.00 (m, 15H), 4.73 (d, J=11.4 Hz, 2H), 4.47 (d, J=11.4 Hz, 2H), 3.92 (s, 4H). $^{13}$C NMR (90 MHz, acetone-d$_6$) δ 144.4, 140.3, 139.9, 134.1, 129.4, 128.7, 127.4, 126.0, 125.6, 125.3, 125.1, 124.9, 124.6, 124.1, 123.2, 123.1, 68.6, 63.9, 54.7.

Example 9

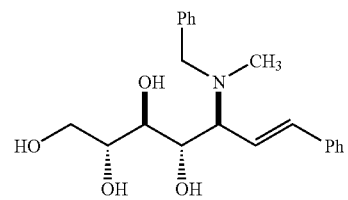

(D)-Ribose (158 mg, 1.05 mmol) was dissolved in EtOH (10 mL) and to this solution was added N-benzyl-methylamine (127 mg, 1.05 mmol), followed by (E)-2-phenylethenyl boronic acid (163 mg, 1.1 mmol). The reaction flask was sealed with a plastic stopper and the reaction mixture was vigorously stirred for 24 hours at ambient temperature. After the removal of volatiles, the residue was redissolved in dichloromethane and purified by flash chromatography on silica gel using dichloromethane-methanol (600:50) as the eluent to obtain 278 mg of pure product (74% yield, >99% de). $^1$H NMR (360 MHz, CD$_3$OD) δ 7.20-7.45 (m, 10H), 6.61 (d, J=16.0 Hz, 1H), 6.33 (dd, J=16.0 Hz, 9.8 Hz, 1H), 3.98 (t, J=8.5 Hz, 1H), 3.65-3.88 (m, 5H), 3.58 (d, J=13.2 Hz, 1H), 3.49 (t, J=8.8 Hz, 1H), 2.25 (s, 3H). $^{13}$C NMR (90 MHz, CD$_3$OD) δ 138.9, 138.0, 137.8, 130.5, 129.6, 129.5, 128.8, 128.6, 127.6, 124.3, 77.2, 75.4, 71.4, 70.8, 64.1, 60.1, 37.9.

Example 10

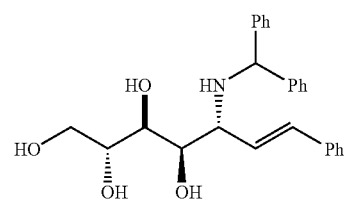

Prepared from (D)-arabinose as in Example 9 in 77% yield, >99% de. $^1$H NMR (360 MHz, CD$_3$OD) δ 7.20-7.43 (m, 15H), 6.34 (d, J=16.2 Hz, 1H), 6.20 (dd, J=16.2 Hz, 8.7 Hz, 1H), 4.98 (s, 1H), 3.88 (m, 2H), 3.77 (dd, J=11.4 Hz, 3.1 Hz, 1H), 3.68 (m, 1H), 3.63 (dd, J=11.4 Hz, 5.9 Hz, 1H), 3.45 (dd, J=8.7 Hz, 5.8 Hz, 1H). $^{13}$C NMR (90 MHz, CD$_3$OD) δ 138.3, 135.0, 129.6, 129.4, 128.9, 128.6, 128.4, 128.2, 128.0, 127.5, 73.2, 73.0, 72.9, 65.1, 64.7, 63.0.

Example 11

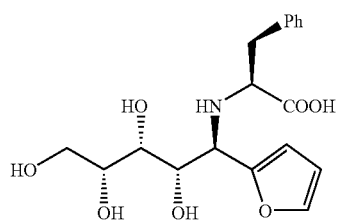

Prepared from (D)-xylose as in Example 9 using 2-furyl boronic acid and phenylalanine as the amine. The reaction was run for 48 hours in MeOH giving the product in 67% yield, >99% de. $^1$H NMR (360 MHz, CD$_3$OD) δ 7.55-7.60 (br, 1H), 7.21-7.38 (m, 5H), 6.43 (br, 2H), 4.27 (m, 1H), 4.05 (m, 1H), 3.50-3.75 (m, 6H), 3.15 (m, 1H). $^{13}$C NMR (90 MHz, CD$_3$OD) δ 173.0, 145.3, 137.6, 130.6, 130.4, 130.0, 128.4, 113.5, 111.9, 72.9, 72.5, 71.6, 64.0, 63.0, 59.9, 37.0.

Example 12

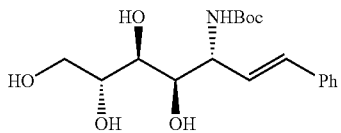

(D)-Arabinose (624 mg, 4.16 mmol) was dissolved in EtOH (15 mL) and to this solution was added 1,1-di-(p-anisyl)methylamine (1,012 mg, 4.16 mmol), followed by (E)-2-phenylethenyl boronic acid (670 mg, 4.53 mmol). The reaction flask was sealed with a plastic stopper and the reaction mixture was vigorously stirred for 24 hours at ambient temperature. The volatiles were removed under vacuum and the residue was heated with 80% acetic acid (10 mL) at 80° C. for 1 hour. Upon cooling, the reaction mixture was diluted with water (20 mL) and further acidified with 3 N hydrochloric acid (10 mL). After the extraction with diethyl ether (3×50 mL), water was evaporated and the resulting residue redissolved in methanol-triethylamine (10:1 by volume, 10 mL). To this solution was added di-tert-butyl dicarbonate (2,200 mg, 10 mmol) and the reaction mixture was heated at 45° C. for 40 min. After the removal of volatiles, pure product was isolated by flash column chromatography on silica gel using dichloromethane-methanol (850:150) as the eluent to give 574 mg of pure product (39% yield for 3 steps, >99% de). $^1$H NMR (360 MHz, CD$_3$OD) δ 7.15-7.42 (m, 5H), 6.57 (d, J=15.9 Hz, 1H), 6.35 (dd, J=15.9 Hz, 5.6 Hz, 1H), 4.38 (m, 1H), 3.58-3.81 (m, 5H), 1.45 (s, 9H). $^{13}$C NMR (90 MHz, CD$_3$OD) δ 158.3, 138.5, 132.2, 129.5, 129.3, 128.4, 127.4, 80.5, 72.7, 72.5, 71.7, 65.0, 56.2, 28.8.

Example 13

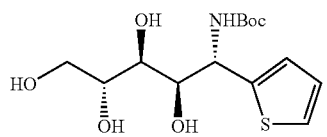

Prepared similarly to Example 12 in 43% overall. $^1$H NMR (360 MHz, CD$_3$OD) δ 7.27 (dd, J=4.7 Hz, 1.0 Hz, 1H), 7.03 (d, 3.7 Hz, 1H), 6.96 (dd, J=4.7 Hz, 3.7 Hz, 1H), 5.05 (d, J=8.3 Hz, 1H), 4.07 (d, J=8.3 Hz, 1H), 3.58-3.81 (m, 4H), 1.43 (s, 9H) $^{13}$C NMR (90 MHz, CD$_3$OD) δ 157.9, 146.0, 127.6, 125.8, 125.1, 80.6, 72.8, 72.7, 71.4, 64.9, 54.5, 28.7.

Example 14

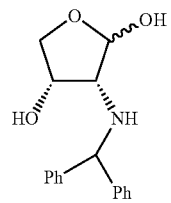

Obtained in 85% yield by ozonolysis of the compound in Example 3 in methanol at −70 C for 5 min with subsequent methyl sulfide workup. The crude product was purified by flash column chromatography on silica gel using dichloromethane-methanol (880:120) as the eluent. $^1$H NMR (360 MHz, DMSO-d$_6$) δ 7.15-7.48 (m, 10H), 5.81-6.09 (m, 1H), 4.95 (s, 1H), 4.89-5.13 (m, 2H), 4.08-4.18 (m, 1H), 3.77-3.91 (m, 1H), 3.58-3.74 (m, 1H), 3.35 (br, 2H), 2.74 (br, 1H). $^{13}$C NMR (90 MHz, DMSO-d$_6$) δ 144.8, 144.5, 144.3, 144.1, 128.4, 128.3, 128.2, 127.2, 127.0, 126.8, 126.7, 101.5, 95.1, 73.2, 72.4, 68.6, 67.4, 65.4, 64.4, 64.0, 60.5.

Example 15

N-(tert-Butoxycarbonyl)-D-mannosamine

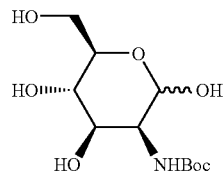

Step 1: (D)-Arabinose (624 mg, 4.16 mmol) was dissolved in EtOH (15 mL) and to this solution was added 1,1-di-(p-anisyl)methylamine (1,012 mg, 4.16 mmol), followed by (E)-2-phenylethenyl boronic acid (670 mg, 4.53 mmol). The reaction flask was sealed with a plastic stopper and the reaction mixture was vigorously stirred for 24 hours at ambient temperature. Volatiles were removed under vacuum and the residue was heated with 80% acetic acid (10 mL) at 80° C. for 1 hour. Upon cooling, the reaction mixture was diluted with water (20 mL) and further acidified with 3N hydrochloric acid (10 mL). After the extraction with diethyl ether (3×50 mL), water was evaporated and the resulting residue redissolved in methanol-triethylamine (10:1 by volume, 10 mL). To this solution was added di-tert-butyl dicarbonate (2,200 mg, 10 mmol) and the reaction mixture was heated at 45° C. for 40 min. After the removal of volatiles, pure product was isolated by flash column chromatography on silica gel using dichloromethane-methanol (850:150) as the eluent. Obtained 574 mg of pure product (39% yield for 3 steps, >99% de). $^1$H NMR (360 MHz, CD$_3$OD) δ 7.15-7.42 (m, 5H), 6.57 (d, J=15.9 Hz, 1H), 6.35 (dd, J=15.9 Hz, 5.6 Hz, 1H), 4.38 (m, 1H), 3.58-3.81 (m, 5H), 1.45 (s, 9H). $^{13}$C NMR (90 MHz, CD$_3$OD) δ 158.3, 138.5, 132.2, 129.5, 129.3, 128.4, 127.4, 80.5, 72.7, 72.5, 71.7, 65.0, 56.2, 28.8.

Step 2: N-(tert-butoxycarbonyl)-D-mannosamine was obtained in 89% yield by ozonolysis of the above compound in methanol at −70° C. for 5 min with subsequent methylsulfide workup. The crude product purified by flash column chromatography on silica gel using dichloromethane-methanol (8:2) as the eluent. $^{13}$C NMR (90 MHz, DMSO-d$_6$) δ 155.9, 155.7, 93.3, 93.0, 77.9, 77.5, 77.2, 72.7, 72.4, 68.3, 66.8, 66.5, 61.2, 60.9, 55.6, 55.2, 48.6, 28.3. HRMS-CI calcd. for C$_{11}$H$_{21}$NO$_7$ (M+H$^+$) 280.1318, found 280.1400

Example 16

N-(tert-Butoxycarbonyl)-D-mannosamine

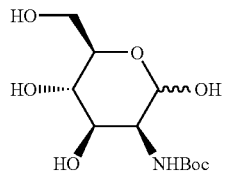

Step 1: D-Arabinose (330 mg, 2.2 mmol) and (E)-phenylethenyl boronic acid (326 mg, 2.2 mmol) were dissolved in MeOH (10 mL) and to this solution was added diallylamine (214 mg, 2.2 mmol). The reaction flask was sealed with a plastic stopper and stirred for 24 hours at ambient temperature. The volatiles were removed under vacuum and the residue was heated with 6N HCl (10 mL) at 50° C. for 45 minutes. Upon cooling to rt, the mixture was diluted with water (10 mL) and washed with dichloromethane (2×10 mL). The aqueous layer was cooled in an ice bath and basified to ~pH 8 with 6N NaOH resulting in a white suspension. This suspension was extracted with EtOAc (3×25 mL) and the organic layers were combined, dried over sodium sulfate, filtered, and concentrated under vacuum to give a thick light-yellow oil. Obtained was 720 mg of crude product which was used without further purification for the next step. (98% crude yield, >99% de and ee.) This compound had satisfactory spectroscopic and analytical data.

Step 2: Pd(dba)$_2$ (80.5 mg, 0.14 mmol, 7 mol %) and DPPB (59.2 mg, 0.14 mmol, 7 mol %) were stirred in 1 mL dry THF in a dry flask under argon at ambient temperature for 15 minutes. Thiosalicylic acid (632 mg, 4.1 mmol, 2.05 eq.) and the crude amino polyalcohol obtained above (720 mg, 2.2 mmol) were dissolved in 4.0 mL THF and added via syringe to the Pd/DPPB mixture. The reaction mixture was heated to 60° C. for 1 hour under an argon atmosphere. The reaction was allowed to cool to room temperature, diluted with EtOAc (20 mL), and the free amine extracted to 2N HCl (2×15 mL). The aqueous layers were combined, washed with EtOAc (1×15 mL), and evaporated to dryness under vacuum to form an amine HCl salt, which had satisfactory spectroscopic and analytical data.

Step 3: The product of Part 2 was dissolved in MeOH (10 mL), treated with excess Et$_3$N (0.25 mL) and Boc$_2$O (650 mg, 3 mmol), and stirred at 50° C. for 45 minutes. After removal of the volatiles under vacuum, the product was purified by flash chromatography on silica gel using MeOH-EtOAc (12:88). Obtained 640 mg white crystalline solid product (83% isolated yield over 3 steps from D-arabinose). This compound had satisfactory spectroscopic and analytical data.

Step 4: The N-Boc-amino tetraol (310 mg, 0.877 mmol) was dissolved in MeOH (30 mL) and cooled to −78° C. Ozone was bubbled through the solution until the blue color persisted (excess ozone was removed by continued bubbling of oxygen until the solution was clear). Excess Me$_2$S (3.0 mL) was added and the solution stirred at −78° C. for 30 minutes, then 0° C. for 30 minutes, and finally warmed to rt and stirred for an additional hour. After removal of the volatiles under vacuum, the residue was chromatographed on silica gel using MeOH—CH$_2$Cl$_2$ (15:85). Obtained 230 mg of pure white N-Boc-D-mannosamine as a mixture of α and β anomers (94% yield). Overall yield from D-arabinose (4 steps) was 78%.

Example 17

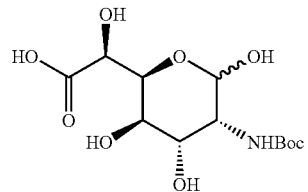

Step 1: D-Gluconic acid (388 mg, 2 mmol) and (E)-2-phenylethenyl boronic acid (296 mg, 2 mmol) were dissolved in MeOH (12 mL) and to this solution was added diallylamine (194 mg, 2 mmol). The reaction flask was sealed with a plastic stopper and stirred for 24 hours at ambient temperature. Volatiles were removed under vacuum and the residue was heated with 6N HCl (10 mL) at 50° C. for 30 minutes. Upon cooling to rt, the mixture was diluted with water (10 mL) and washed with EtOAc (2×15 mL). The aqueous layer was cooled in an ice bath and carefully neutralized with 6N NaOH to form a white suspension. This aqueous suspension was extracted with EtOAc (3×20 mL). The organic layers were combined, washed with brine (2×15 mL), dried over sodium sulfate, filtered, and evaporated to give 612 mg of white flaky solid product. No further purification was necessary. (83% yield, >99% de and ee). $^1$H NMR (360 MHz, CD$_3$OD) δ 7.18-7.26 (m, 1H), 7.27-7.34 (m, 2H), 7.39-7.46 (m, 2H) 6.54 (d, J=16.2 Hz, 1H), 6.35 (dd, J=16.2 Hz, 9.4 Hz, 1H), 5.87 (m, 2H), 5.12-5.27 (m, 4H), 4.51 (d, J=4.6 Hz, 1H), 4.38-4.45 (m, 2H), 4.26-4.31 (t, J=6.1 Hz, 1H), 3.56 (dd, J=9.4 Hz, 6.1 Hz, 1H), 3.48 (dd, J=14.1 Hz, 4.6 Hz, 2H), 3.04 (dd, J=14.1 Hz, 8.0 Hz, 2H). $^{13}$C NMR (90 MHz, CD$_3$OD) δ 178.0, 138.1, 136.90, 136.88, 129.6, 128.8, 127.5, 125.3, 118.7, 83.2, 72.2, 71.7, 71.1, 64.1, 54.6.

Step 2: Pd(dba)$_2$ (40.25 mg, 0.07 mmol, 7 mol %) and DPPB (29.90 mg, 0.07 mmol, 7 mol %) were stirred in 1 mL dry THF in a dry flask under argon at ambient temperature for 15 minutes. Thiosalicylic acid (316 mg, 2.05 mmol, 2.05 eq.) and the amino acid substrate (377 mg, 1 mmol) were dissolved in 2.5 mL THF and added via syringe to the Pd/DPPB mixture. The reaction mixture was heated to 60° C. for 3 hours under an argon atmosphere. The reaction was allowed to cool to room temperature, diluted with EtOAc (20 mL), and the free amine extracted to 2N HCl (2×15 mL). The aqueous layers were combined, washed with EtOAc (1×15 mL), and evaporated to dryness under vacuum to form a free amine HCl salt.

Step 3: The product of Step 2 was dissolved in water-dioxane (10 mL, 1:1) and treated with NaHCO$_3$ (168 mg, 2 mmol) and Boc$_2$O (300 mg, 1.38 mmol). The reaction was sealed and stirred for 12 hours. The mixture was carefully acidified to pH 2 with 2N HCl and extracted with EtOAc (4×20 mL). The organic layers were combined, dried over sodium sulfate, filtered, and evaporated under vacuum. The product was purified by flash chromatography on silica gel using dichloromethane-methanol (9:1). Obtained 264 mg white crystalline product (67% yield for 2 steps, >99% de and ee). $^1$H NMR (360 MHz, CD$_3$OD) δ 7.37-7.47 (m, 2H), 7.16-7.36 (m, 3H), 6.64 (d, J=16 Hz, 1H), 6.32 (dd, J=16 Hz, 8.0 Hz, 1H), 4.38-4.52 (m, 3H), 4.25 (dd, J=8.0 Hz, 2.9 Hz, 1H), 4.10 (dd, J=8.0 Hz, 3.5 Hz, 1H), 1.44 (s, 9H). $^{13}$C NMR (90 MHz, CD$_3$OD) δ 177.8, 157.4, 138.1, 134.2, 129.6, 128.8, 127.6, 126.4, 82.5, 80.6, 73.1, 72.2, 70.7, 55.1, 28.7.

Step 4: The N-Boc-amino acid (120 mg, 0.30 mmol) was dissolved in MeOH (20 mL) and cooled to −78° C. Ozone was bubbled through the solution until the blue color persisted (excess ozone was removed by continued bubbling of oxygen until the solution was clear). Excess Me$_2$S (1.2 mL) was added and the solution stirred at −78° C. for 30 minutes, then 0° C. for 30 minutes, and finally warmed to rt and stirred for an additional hour. After removal of the volatiles under vacuum, diethyl ether (50 mL) was added and the mixture stirred for 15 minutes. The resulting white precipitate was filtered, washed with diethyl ether (2×30 mL), and dried under a constant stream of dry nitrogen (product is hygroscopic). Obtained 85 mg of pure white fluffy product as a mixture of α and β anomers (88% yield). Overall yield from D-gluconic acid (4 steps) was 49%. $^1$H NMR (360 MHz, DMSO-d$_6$) δ 6.70 (d, J=6.2 Hz, 0.4H), 6.65 (d, J=6.2 Hz, 0.6H), 6.42 (d, J=9.2 Hz, 0.4H), 6.33 (d, J=9.2 Hz, 0.6H), 5.89-5.95 (m, 1H), 5.61 (d, J=4.5 Hz, 0.4H), 5.27 (d, J=6.2 Hz, 0.6H), 4.90-4.96 (m, 0.6H), 4.77 (t, J=7.5 Hz, 0.4H), 4.65 (dd, J=7.9 Hz, 3.9 Hz, 0.6H), 4.60 (dd, J=7.4 Hz, 3.9 Hz, 0.4H), 4.47 (bs, 0.6H), 4.30-4.39 (m, 1H), 4.22 (bs, 0.4H), 3.86-3.97 (m, 1H), 3.46-3.54 (m, 0.6H), 3.34-3.41 (m, 0.4H), 1.38 (s, 5.4H), 1.37 (s, 3.6H). $^{13}$C NMR (90 MHz, DMSO-d$_6$) δ 175.48, 175.43, 155.17, 155.01, 90.95, 90.57, 78.51, 77.81, 75.62, 75.59, 71.83, 70.62, 70.52, 66.16, 65.07, 64.88, 52.00, 47.35, 28.25, 28.12.

A number of embodiments of the invention have been described. Nevertheless, it will be understood that various modifications may be made without departing from the spirit and scope of the invention. Accordingly, other embodiments are within the scope of the following claims.

What is claimed is:
1. A compound of formula 4:

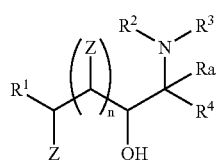

4 wherein:
n is an integer from 0-4;
Ra is hydrogen, alkyl, alkenyl, alkynyl, allenyl, aryl, heteroaryl, acyl, carboxyalkyl, or carboxyaryl;

R$^1$ is hydrogen, alkyl, alkenyl, alkynyl, allenyl, aryl or heteroaryl;
R$^2$ and R$^3$ are independently selected from the group consisting of hydrogen, alkyl, aryl, hydroxy, alkoxy, acyl, carboxyalkyl, carboxamido, alkylamino, dialkylamino, acylamino, silyl, phosphinyl, sulfonyl, sulfinyl, and alkylsulfonate, provided that R$^2$ and R$^3$ can be joined together to form one or more rings;
the Z substituents are independently selected from the group consisting of hydroxy, hydrogen, and —OR, where R is aryl, silyl, acyl, alkoxyacyl, aminoacyl, or unsubstituted alkyl, provided that Z can exist as an acetal or ketal and provided that at least one Z substituent is hydroxy or —OR,
wherein either
R$^4$ is alkenyl; alkynyl; allenyl; substituted phenyl; phenyl fused to an aryl or cycloalky ring; or napthyl; or
R$^4$ is alkenyl, alkynyl, allenyl, or aryl, and one or more of R$^2$ or R$^3$ is allyl or substituted allyl.
2. A compound of formula 4:

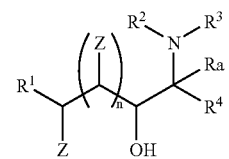

4 wherein:
n is an integer from 0-4;
Ra is hydrogen, alkyl, alkenyl, alkynyl, allenyl, aryl, heteroaryl, acyl, carboxyalkyl, or carboxyaryl;
R$^1$ is hydrogen, alkyl, alkenyl, alkynyl, allenyl, aryl or heteroaryl;
R$^2$ and R$^3$ are independently selected from the group consisting of hydrogen, alkyl, aryl, heteroaryl, hydroxy, alkoxy, acyl, carboxyalkyl, carboxamido, alkylamino, dialkylamino, acylamino, silyl, phosphinyl, sulfonyl, sulfinyl, and alkylsulfonate, provided that R$^2$ and R$^3$ can be joined together to form one or more rings;
the Z substituents are independently selected from the group consisting of hydroxy, hydrogen, alkyl, alkenyl, alkynyl, allenyl, aryl, heteroaryl, acyl, oxo, carboxy, carboxyalkyl, carboxyaryl, carboxamido, dialkylamino, acylamino, cyano, sulfonylamino, carbamate, acetal, ketal, borate, boronate, 3-7 membered heterocycle, and —OR, where R is alkyl, aryl, heteroaryl, silyl, acyl, alkoxyacyl or aminoacyl, provided that at least one Z substituent is hydroxy or —OR and that, when n=1-4, at least one Z substituent is not hydrogen, hydroxy, acetal, ketal or —OR,
wherein either
R$^4$ is alkenyl; alkynyl; allenyl; substituted phenyl; phenyl fused to an aryl or cycloalky ring; or napthyl; or heteroaryl; or
R$^4$ is alkenyl, alkynyl, allenyl, aryl or heteroaryl, and one or more of R$^2$ or R$^3$ is allyl or substituted allyl.
3. A method for preparing the amino polyol of claims 1 or 2, comprising:
providing a carbohydrate;
providing an amine;
providing an organoboron derivative; and
allowing the carbohydrate, amine and organoboron derivative to react to form an aminopolyol.

4. A method for preparing the amino polyol of claims 1 or 2, the method comprising providing a carbohydrate of formula 1a or 1b:

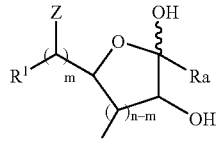

1a

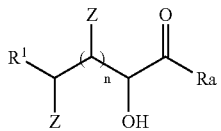

1b wherein:
- n and m are integers from 0-4 and n is greater than or equal to m;
- Ra is hydrogen, alkyl, alkenyl, alkynyl, allenyl, aryl, heteroaryl, acyl, carboxyalkyl, or carboxyaryl;
- $R^1$ is hydrogen, alkyl, alkenyl, alkynyl, allenyl, aryl or heteroaryl; and
- the Z substituents are independently selected from the group consisting of hydroxy, hydrogen, and —OR, where R is alkyl, aryl, silyl, acyl, alkoxyacyl or aminoacyl, provided that Z can exist as an acetal or ketal and provided that at least one Z substituent in the carbohydrate of formula 1a or 1b must be hydroxy or —OR;

providing an amine of formula 2

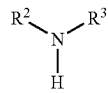

2 wherein:
- $R^2$ and $R^3$ are independently selected from the group consisting of hydrogen, alkyl, aryl, hydroxy, alkoxy, acyl, carboxyalkyl, carboxamido, alkylamino, dialkylamino, acylamino, silyl, phosphinyl, sulfonyl, sulfinyl, and alkylsulfonate, provided that $R^2$ and $R^3$ can be joined together to form one or more rings of 2 to 20 atoms;

providing an organoboron derivative of formula 3

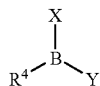

3 wherein:
- $R^4$ is alkenyl, alkynyl, allenyl, or aryl;
- X and Y are independently selected from hydroxy, alkoxy, aryloxy, halo, amino, alkylamino, dialkylamino, alkyl or aryl, provided that the organoboron derivative can include a fourth boron substituent selected from hydroxy, alkoxy, dialkylamino and halo; and
- allowing the carbohydrate, amine and organoboron derivative to react to form an amino polyol product of formula 4:

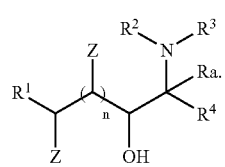

4

5. The method of claim 4, wherein the carbohydrate of formula 2, the amine of formula 2 or the organoboron compound of formula 3 is attached to a polymer or other solid support.

6. The method of claim 5, further comprising treating the aminopolyol product of formula 4 to form an amino sugar of formula 11a or 11b or formula 12a or 12b:

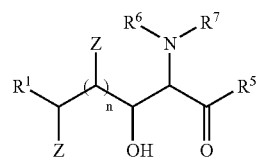

11a

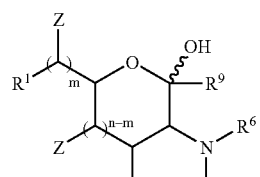

11b

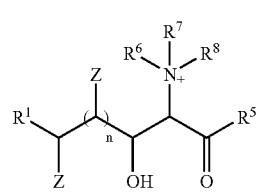

12a

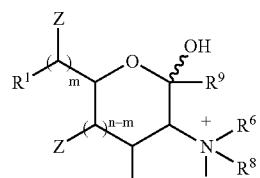

12b wherein:
- $R^6$ and $R^7$ are independently selected from the group consisting of hydrogen, acyl, alkoxyacyl, aminoacyl, carbamate, sulfonyl, sulfinyl, phosphonate and sulfonate, provided that $R^6$ and $R^7$ can be the same as substituents $R^2$ or $R^3$ and further provided that $R^6$ and $R^7$ can be joined together to form one or more rings;
- $R^8$ hydrogen, alkyl or acyl; and
- $R^9$ is hydrogen, alkyl, alkenyl, alkynyl, allenyl, aryl, heteroaryl, acyl, carboxyalkyl, or carboxyaryl.

7. The method of claim 6, wherein treating the aminopolyol product includes forming a protected amine and treating the protected amine with a cleaving agent to generate a carbonyl group.

8. The method of claim 6, wherein one or more of $R^2$ or $R^3$ is benzyl or substituted benzyl.

9. The method of claim 6, wherein the amine of formula 2 is 1,1-di(p-anisyl)methylamine.

10. The method of claim 6, wherein one or more of $R^2$ or $R^3$ is allyl or substituted allyl.

11. The method of claim 6, wherein the amine of formula 2 is diallylamine.

12. The method of claim 4, further comprising treating the aminopolyol product of formula 4 to form an amino sugar of formula 11a or 11b or formula 12a or 12b;

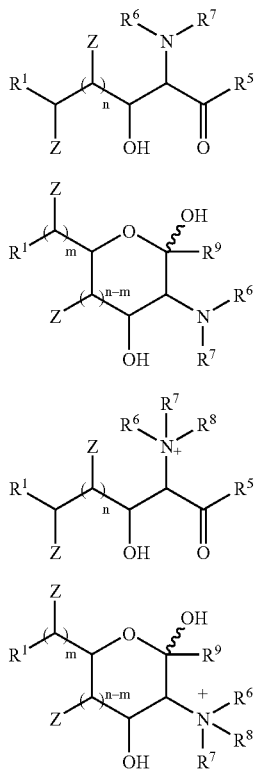

wherein:

R⁶ and R⁷ are independently selected from the group consisting of hydrogen, acyl, alkoxyacyl, aminoacyl, carbamate, sulfonyl, sulfinyl, phosphonate and sulfonate, provided that $R^6$ and $R^7$ can be the same as substituents $R^2$ or $R^3$ and further provided that $R^6$ and $R^7$ can be joined together to form one or more rings;

$R^8$ is hydrogen, alkyl or acyl; and $R^9$ is hydrogen, alkyl, alkenyl, alkynyl, allenyl, aryl, heteroaryl, acyl, carboxyalkyl, or carboxyaryl.

13. The method of claim 12, wherein treating the aminopolyol product includes forming a protected amine and treating the protected amine with a cleaving agent to generate a carbonyl group.

14. The method of claim 12, wherein one or more of $R^2$ or $R^3$ is benzyl or substituted benzyl.

15. The method of claim 12, wherein the amine of formula 2 is 1,1-di(p-anisyl)methylamine.

16. The method of claim 12, wherein one or more of $R^2$ or $R^3$ is allyl or substituted allyl.

17. The method of claim 12, wherein the amine of formula 2 is diallylamine.

18. The method of claim 4, wherein the amino polyol is formed in predominantly one stereoisomer having the amino group in an anti-relationship to the adjacent hydroxyl group.

19. The method of claim 4, further comprising:

treating the amino polyol product to protect the amino group; and oxidizing the polyol to generate a protected amino acid.

* * * * *

UNITED STATES PATENT AND TRADEMARK OFFICE
CERTIFICATE OF CORRECTION

PATENT NO. : 7,462,746 B2
APPLICATION NO. : 10/405922
DATED : December 9, 2008
INVENTOR(S) : Nicos A. Petasis, Ilia A. Zavialov and Zubin D. Patel It is certified that error appears in the above-identified patent and that said Letters Patent is hereby corrected as shown below:

Column 20, Line 8 at Claim 1; replace:
"together to form one or more rings;" with
-- together to form one or more rings; and --

Column 20, Line 17 at Claim 1; replace:
"fused to an aryl or cycloalky ring; or napthyl; or" with
-- fused to an aryl or cycloalkyl ring; or napthyl; or --

Column 20, Line 43 at Claim 2; replace:
"be joined together to form one or more rings;" with
-- be joined together to form one or more rings; and --

Column 20, Line 50 at Claim 2; replace:
"alkoxyacyl or aminoacyl, provided that at least one Z" with
-- alkoxyacyl, or aminoacyl, provided that at least one Z --

Column 20, Line 53 at Claim 2; replace:
"ketal or OR," with
-- ketal or –OR, --

Column 20, Line 56 at Claim 2; replace:
"fused to an aryl or cycloalky ring; or napthyl; or het-" with
-- fused to an aryl or cycloalkyl ring; napthyl; or het- --

Column 22, Line 49 at Claim 6; replace:
"$R^8$ hydrogen, alkyl or acyl; and" with
-- $R^8$ is hydrogen, alkyl or acyl; and --

UNITED STATES PATENT AND TRADEMARK OFFICE
CERTIFICATE OF CORRECTION

PATENT NO.         : 7,462,746 B2
APPLICATION NO. : 10/405922
DATED               : December 9, 2008
INVENTOR(S)       : Nicos A. Petasis, Ilia A. Zavialov and Zubin D. Patel It is certified that error appears in the above-identified patent and that said Letters Patent is hereby corrected as shown below:

Column 22, Line 67 at Claim 12; replace:
"formula 11a or 11b or formula 12a or 12b;" with
-- formula 11a or 11b or formula 12a or 12b: --

Signed and Sealed this

Seventh Day of April, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,462,746 B2 |
| APPLICATION NO. | : 10/405922 |
| DATED | : December 9, 2008 |
| INVENTOR(S) | : Nicos A. Petasis, Ilia A. Zavialov and Zubin D. Patel |

Page 1 of 1

It is certified that error appears in the above-identified patent and that said Letters Patent is hereby corrected as shown below:

Column 1, lines 24-26, delete "The U.S. Government may have certain rights in this invention pursuant to Grant No. GM45970 awarded by the National Institutes of Health" and insert --This invention was made with government support under Contract No. GM045970 awarded by the National Institutes of Health. The government has certain rights in the invention--.

Signed and Sealed this

Thirtieth Day of June, 2009

JOHN DOLL
*Acting Director of the United States Patent and Trademark Office*